US012564519B2

(12) United States Patent
Merckel et al.

(10) Patent No.: US 12,564,519 B2
(45) Date of Patent: *Mar. 3, 2026

(54) SUPERABSORBENT WOUND DRESSING WITH SILICONE WOUND CONTACT LAYER

(71) Applicant: PAUL HARTMANN AG, Heidenheim (DE)

(72) Inventors: Fabien Merckel, Straßbourg (FR); Renaud Thiebaut, Chatenois (FR)

(73) Assignee: PAUL HARTMANN AG, Heidenheim (DE)

( * ) Notice: Subject to any disclaimer, the term of this patent is extended or adjusted under 35 U.S.C. 154(b) by 569 days.

This patent is subject to a terminal disclaimer.

(21) Appl. No.: 17/415,228

(22) PCT Filed: Dec. 13, 2019

(86) PCT No.: PCT/EP2019/085061
§ 371 (c)(1),
(2) Date: Jun. 17, 2021

(87) PCT Pub. No.: WO2020/126900
PCT Pub. Date: Jun. 25, 2020

(65) Prior Publication Data
US 2022/0062059 A1     Mar. 3, 2022

(30) Foreign Application Priority Data

Dec. 21, 2018     (EP) ..................................... 18215471

(51) Int. Cl.
A61F 13/0206     (2024.01)
A61F 13/0203     (2024.01)
A61F 13/0246     (2024.01)
(52) U.S. Cl.
CPC ........ *A61F 13/0209* (2013.01); *A61F 13/022* (2013.01); *A61F 13/0223* (2013.01); *A61F 13/025* (2013.01); *A61F 13/0253* (2013.01)

(58) Field of Classification Search
CPC ..................... A61F 2013/00655–00719; A61F 13/00–0293; A61F 2013/00238;
(Continued)

(56) References Cited

U.S. PATENT DOCUMENTS 6,566,577 B1     5/2003   Addison et al.
6,903,243 B1     6/2005   Burton
(Continued)

FOREIGN PATENT DOCUMENTS

AU         2007304309 B2     4/2008
CN            101002707 A     7/2007
(Continued)

OTHER PUBLICATIONS

"Technical Information", Mepilex Border Product Manual, Apr. 2012, pp. 1-4; Retrieved on Apr. 4, 2017 from the Internet.
(Continued)

*Primary Examiner* — Michelle J Lee
(74) *Attorney, Agent, or Firm* — LEYDIG, VOIT & MAYER, LTD.

(57)     ABSTRACT

Wound dressing (10, 20) comprising a backing layer (11, 21), an absorbent pad (12, 22), and a wound contact layer (13, 23), the absorbent pad (12, 22) having an absorbent core (15, 25) wherein the backing layer (11, 21) comprises a water vapour-permeable and substantially liquid-impermeable film material, wherein the wound contact layer (13, 23) comprises a layer of skin-friendly silicone adhesive (13b, 23b), the wound contact layer (13, 23) comprising apertures (13c, 23c), each of the apertures (13c, 23c) having an average area of from 0,03 mm² to 7,00 mm², and the entire open area of the wound contact layer (13, 23) formed by the apertures (13c, 23c) is between 10% and 30%, characterized in that a distribution layer (14a, 24a) is arranged between the wound contact layer (13, 23) and the absorbent core (15, 25).

18 Claims, 2 Drawing Sheets

(58) Field of Classification Search
CPC ..................... A61F 2013/00246–00263; A61F
2013/00744; A61F 2013/00748–00757;
A61F 2013/00855–00868; A61F
2013/15495; A61F 2013/15544–15569;
A61F 13/02–0293; A61F 2013/00089;
A61F 2013/00102; A61F
2013/00361–00982
See application file for complete search history.

(56) References Cited

U.S. PATENT DOCUMENTS

| | | | |
|---|---|---|---|
| 8,247,635 | B2 | 8/2012 | Sigurjonsson et al. |
| 9,452,086 | B2 | 9/2016 | Auguste et al. |
| 2003/0064190 | A1* | 4/2003 | Carte ..................... B32B 3/266 |
| | | | 156/289 |
| 2003/0125680 | A1* | 7/2003 | Ding ................... A61F 13/0203 |
| | | | 602/54 |
| 2008/0171958 | A1* | 7/2008 | Gundersen ........... A61F 13/022 |
| | | | 602/56 |
| 2009/0216168 | A1* | 8/2009 | Eckstein ................. A61L 15/60 |
| | | | 602/43 |
| 2010/0069850 | A1* | 3/2010 | Fabo ....................... A61M 1/87 |
| | | | 604/180 |
| 2010/0159192 | A1* | 6/2010 | Cotton .................... A61L 15/58 |
| | | | 428/137 |
| 2010/0331785 | A1 | 12/2010 | Fabo et al. |
| 2011/0130738 | A1 | 6/2011 | Schmidt |
| 2011/0313383 | A1* | 12/2011 | Hofstetter .............. A61F 13/00 |
| | | | 604/372 |
| 2012/0095380 | A1 | 4/2012 | Gergely et al. |
| 2013/0012902 | A1 | 1/2013 | Rovaniemi |
| 2014/0114268 | A1* | 4/2014 | Auguste ................ A61F 13/022 |
| | | | 156/182 |
| 2014/0142526 | A1 | 5/2014 | Auguste et al. |
| 2014/0350494 | A1 | 11/2014 | Hartwell et al. |
| 2016/0067107 | A1* | 3/2016 | Cotton .................... A61L 15/28 |
| | | | 602/44 |
| 2016/0331603 | A1* | 11/2016 | Revol-Cavalier ........................... |
| | | | A61F 13/53717 |
| 2017/0181897 | A1 | 6/2017 | Hartwell |
| 2018/0071147 | A1* | 3/2018 | Marz ................. A61F 13/01029 |
| 2018/0125722 | A1 | 5/2018 | Hoggarth et al. |
| 2018/0361013 | A1 | 12/2018 | Cotton |
| 2019/0133830 | A1 | 5/2019 | Bishop et al. |
| 2019/0274889 | A1 | 9/2019 | Steward et al. |

FOREIGN PATENT DOCUMENTS

| | | | | |
|---|---|---|---|---|
| CN | 104523369 | A * | 4/2015 | ....... A61F 13/00021 |
| CN | 205181608 | U | 4/2016 | |
| CN | 106510952 | A | 3/2017 | |
| CN | 107669405 | A | 2/2018 | |
| DE | 3718076 | A1 | 12/1987 | |
| DE | 102007049428 | A1 | 4/2009 | |
| DE | 102008062824 | A1 | 7/2010 | |
| EP | 0237990 | B1 | 9/1987 | |
| EP | 0681820 | B1 | 11/1995 | |
| EP | 1985270 | A2 | 10/2008 | |
| EP | 2001424 | B1 | 11/2011 | |
| EP | 2039328 | B1 | 3/2014 | |
| EP | 3146964 | A1 * | 3/2017 | ............ A61K 47/10 |
| EP | 3338813 | A1 | 6/2018 | |
| EP | 3338813 | B1 | 1/2020 | |
| GB | 1280631 | A | 7/1972 | |
| GB | 2379392 | A | 3/2003 | |
| GB | 2512841 | A | 10/2014 | |
| GB | 2531344 | A | 4/2016 | |
| SE | 0901356 | A1 * | 4/2011 | |
| WO | 93/19709 | | 10/1993 | |
| WO | 93/19710 | | 10/1993 | |
| WO | WO-2006075949 | A1 * | 7/2006 | ............ A61F 5/443 |
| WO | WO-2007092350 | A1 * | 8/2007 | .......... A61F 13/023 |
| WO | 2010147533 | A1 | 12/2010 | |
| WO | WO 2014/020440 | A1 | 2/2014 | |
| WO | 2014/097069 | A1 | 6/2014 | |
| WO | WO 2014/167307 | A1 | 10/2014 | |
| WO | WO 2016/038109 | A1 | 3/2016 | |
| WO | WO 2017138962 | A1 | 8/2017 | |
| WO | 2017196888 | A1 | 11/2017 | |
| WO | 2018077872 | A1 | 5/2018 | |

OTHER PUBLICATIONS

International Search Report and Written Opinion from PCT/EP2019/
085061 mailed Mar. 24, 2020.
Communication from European Patent Office, Opposition Division,
for EP application No. 18 215 471.6, Mar. 19, 2025, 6 pages.
Allevyn Wound Dressings, Smith & Nephew website, http://wound.
smith-nephew.com/de/Standard.asp?Nodeid=3284, and related wound
dressing products from 2009-2013 submitted in opposition proceed-
ing for EP application No. 18 215 471.6, 7 pages.
ExpressMed, "How to Apply Mepilex® Border", screenshots from
Youtube.com, Nov. 13, 2017, submitted in opposition proceeding
for EP application No. 18 215 471.6, 2 pages.
Molnlycke Healthcare, Mextra Superabsorbent wound dressing, US
product catalog, 270481, Sep. 2017, 2 pages.
Molnlycke Healthcare, Mextra Superabsorbent wound dressing, UK
product catalog, UKWC0449, 2018, 2 pages.
Molnlycke Healthcare, photo of Mextra Superabsorbent wound
dressing product, Lot 17407896, Sep. 28, 2020, and packing slip for
Mextra Superabsorbent and Mepilex products, Jun. 11, 2018, sub-
mitted in opposition proceeding for EP application No. 18 215
471.6, 2 pages.
NHS, NHS Clinical Evaluation Team, Clinical Review—Foam
Dressings, Oct. 2018, 92 pages.

* cited by examiner

SUPERABSORBENT WOUND DRESSING WITH SILICONE WOUND CONTACT LAYER

This application claims priority to European Patent Application No. 18215471.6 filed on Dec. 21, 2018.

DESCRIPTION

The present invention deals with an absorbent wound dressing, in particular for the treatment of chronic wounds.

Absorbent wound dressings have been used in the treatment of wounds for several years. Ideal wound dressings must fulfill multiple tasks that sometimes are difficult or impossible to optimize simultaneously. They must be capable to absorb high amounts of wound exudate in a rapid and complete manner, providing a wound-healing supporting environment, while preventing leakage of wound exudate during treatment. They must be able to adhere to intact human or animal skin without irritating the wound tissue or the intact skin surrounding the wound and must exhibit atraumatic properties, i.e. they must be displaced from the wound without causing pain or irritation. They must provide a barrier against external dust, moisture and microorganisms, but have to be moisture-permeable in order to enable sufficient gas and vapor exchange between the wound and the environment. The dressings must exhibit comfortable wearing properties, i.e. they must be flexible and capable of adapting to different skin regions of the body thereby not causing pain or unpleasant feeling during the treatment. Furthermore, they should be able to be worn for up to seven days without dressing change.

Currently, no wound dressing is available on the market which exhibits each of these properties in a perfect matter.

WO93/19709 discloses a method and an arrangement for manufacturing wound dressings, wherein the wound dressings comprise a perforated wound contact layer made from an adhesive silicone.

WO93/19710 discloses a wound dressing comprising a backing layer, an absorbent pad and a wound contact layer, wherein the wound contact layer comprises a perforated layer of adhesive silicone.

WO2014/097069 discloses a wound dressing comprising a backing layer, an absorbent island and an apertured wound contact layer.

There is a strong need for improvements of one or more of the mentioned properties in the development of wound dressings, in particular in the treatment of chronic wounds.

The invention according to claim 1 solves the aforementioned problems.

The wound dressing comprises a backing layer, an absorbent pad, a wound contact layer and a distribution layer that is arranged between the absorbent core and the wound contact layer. The absorbent pad has an absorbent core.

In the present application the terms proximal side or proximal surface are to be understood as that side or surface of a layer or material of the wound dressing that is in use facing a wound. The terms distal side or distal surface are to be understood as that side or surface of a layer or material that is in use facing away from the wound.

The backing layer may have any shape, such as square, rectangular, circular, oval, trapezium-shaped, suitably with rounded corners.

The backing layer supports the absorbent pad and provides a barrier to passage of microorganisms through the dressing. The backing layer is substantially liquid-impermeable but permeable for water vapor, suitably in form of a film material. The backing layer suitably has a moisture vapour transmission rate (MVTR) from 300 to 30000 g/m$^2$/24 h, suitably 1000 to 15000 g/m$^2$/24 h, and in one embodiment 1000 to 5000 g/m$^2$/24 h according to test method EN 13726. The backing layer has a thickness of 10 μm to 100 μm, suitably 12 μm to 75 μm, and in a preferred embodiment 15 μm to 50 μm, most preferred 25 μm to 35 μm. The backing layer comprises a proximal surface and a distal surface. The distal surface of the backing layer suitably is a low-friction surface in order to exhibit advantageous wearing properties without sticking to clothes or causing noise during use.

Suitable polymers for forming the backing layer material include polyurethanes, poly alkoxyalkyl acrylates and methyl acrylates such as those disclosed in GB1280631. Suitably, the backing layer comprises a continuous layer of a high density blocked polyurethane foam that is predominantly closed-cell. A suitable backing layer material is the polyurethane film available as film number 1305 from the company Coveris, having a thickness of 30 μm.

Preferably, the backing layer is transparent in order to allow a view of the absorbent pad positioned on the proximal side of the backing layer.

The backing layer can be coated with an adhesive on the proximal surface. The adhesive secures the backing layer to further layers of the wound dressing, particularly to the absorbent pad and to the wound contact layer. The backing layer can be coated with adhesive continuously, i.e. the adhesive covers the entire proximal surface of the backing layer. In different embodiments, the backing layer can be coated partially with adhesive. In these embodiments the adhesive can be in the form of stripes, dots or in different patterns. In a further embodiment the backing layer comprises an adhesive layer on the proximal surface that leaves an adhesive-free part in the center of the backing layer to reduce contact with the distal surface of the absorbent pad. The MVTR in an adhesive-free region of the backing layer is increased. If the absorbent core within the absorbent pad swells after absorption of wound exudate the absorbent pad changes its spatial extension. This can either cause delamination due to the occurrence of shearing forces within the wound dressing, or it can cause stress and pain on the wound and/or the wound surrounding skin due to shearing forces acting on the wound and skin of the patient. A dressing leaving an adhesive-free area between the distal surface of the absorbent pad and the proximal surface of the backing layer can be advantageous in this respect.

The adhesive preferably is a pressure-sensitive adhesive of the type that is conventionally used for medical dressings. Suitable pressure-sensitive adhesives can be based on acrylic acid, acrylate ester copolymers, polyvinyl ethyl ether and polyurethane such as those described in GB1280631. The basis weight of the pressure-sensitive adhesive is suitably 10 g/m$^2$ to 100 g/m$^2$, preferably 15 g/m$^2$ to 50 g/m$^2$, more preferably 20 g/m$^2$ to 30 g/m$^2$ The absorbent pad comprises an absorbent material. Suitable absorbent materials comprise fibers, absorbent particles, foams, sponges, gels, derived from natural or synthetic sources. Suitable materials include, but are not limited to, cellulose, viscose, carboxymethyl cellulose, other cellulose-based polymers, polyester, polyamide, polyacrylate, polyvinyl alcohol, polyurethane, polyurea, polyoxyalkylene like polyoxyethylene or polyoxypropylene, polyalkylene like polyethylene or polypropylene, derivatives, copolymers and mixtures thereof.

A distribution layer is a layer comprising a material that is capable of uptaking wound exudate from a wound, spreading the exudate within the distribution layer and transmitting the exudate from the proximal surface of the distribution layer to the distal surface of the distribution layer in an efficient manner. Preferably, a distribution layer has a lower absorption capacity than the absorbent core. In particular, a suitable distribution layer has an absorption capacity that is less than 80% of the absorption capacity of the absorbent core, preferably less than 60%, more preferably less than 40%, most preferably less than 20%. Absorption capacity can be determined according to a procedure described in the example part of this application. It was unexpectedly found that providing a wound dressing with a distribution layer arranged between the absorbent core and the wound contact layer, the absorption velocity increases. Absorption velocity can be determined according to a method described in the example part of this application.

A suitable distribution layer can comprise nonwoven materials, woven materials, warp-knitted textiles, weft-knitted textiles, foils or films.

Suitable materials for a distribution layer include but are not limited to cellulose, viscose, other cellulose-based polymers, polyester, polyamide, polyurethane, polyurea, polyoxypropylene, polyalkylene.

Preferred material for a distribution layer is a nonwoven material made from a mixture of polyamide and viscose fibers.

In a preferred embodiment the distribution layer and the wound contact layer are connected to each other. If both layers are connected to each other, the movability of each layer in respect to the other is decreased. This results in defined zones within the distribution layer which can be directly in contact with wound exudate, i.e. those parts of the distribution layer facing an aperture of the wound contact layer, and in defined zones within the distribution layer that only can be indirectly in contact with wound exudate via diffusion within the distribution layer. This kind of zones that are not directly in contact with wound exudate enhance the capability of lateral distribution of exudate within the distribution layer and therefore have an advantageous effect on the absorption velocity. Suitable connection means include adhesives, preferably pressure-sensitive adhesives like polyacrylate-based adhesives.

The absorbent pad can essentially consist of an absorbent core or can comprise further layers and materials.

Preferably, the absorbent pad comprises an absorbent core comprising any of the mentioned materials, and an envelope surrounding the absorbent core. The distribution layer may be a part of the envelope.

The absorbent core has a proximal side and a distal side. The absorbent core comprises an absorbent material. An absorbent is capable of absorbing liquids such as wound exudate. The material can comprise any wound exudate-absorbing material, particularly absorbent fibers and/or absorbent particles.

Suitably, the material comprises a mixture of absorbent fibers and absorbent particles.

Suitable materials for absorbent fibers can be cellulose or cellulose-based polymers, viscose, polyester, polyamide, derivatives, copolymers and mixtures thereof. Furthermore, suitable fibers include superabsorbent fibers that can be based on polyacrylic acid, sodium polyacrylate, polyacrylic acid esters, copolymers and mixtures thereof. A preferred material is cellulose.

Suitable materials for absorbent particles include, but are not limited to, superabsorbent particles. Suitable materials for superabsorbent particles include, but are not limited to, polyacrylic acid, sodium polyacrylate, polyacrylic acid esters, copolymers and mixtures thereof. A preferred material is sodium polyacrylate.

In a preferred embodiment, the absorbent core comprises a mixture of absorbent fibers consisting essentially of cellulose and superabsorbent particles made from polyacrylic acid and sodium polyacrylate. Such an absorbent core exhibits its rapid absorption of wound exudate and rapid distribution within the absorbent core.

The superabsorbent material can be present in an amount of from 1% by weight to 99% by weight within the absorbent core. Preferably, the amount of superabsorbent material comprises from 30% to 55% by weight of the absorbent core.

A superabsorbent material is generally understood to be a water-insoluble, swellable polymer that can absorb a multiple of its own weight of liquid such as water, saline solutions, or body fluids. The absorption of liquid results in the formation of a hydrogel. The absorption capacity for pure water is typically greater than the absorption capacity for saline liquid. In connection with this invention, the term superabsorbent material refers, in particular, to a material exhibiting a w value (free swell capacity) according to the standard test method WSP 240.2 (05) of at least 10 g/g, preferably at least 20 g/g. The test method WSP 240.2 (05) for determining the w value is described in "Standard Test Methods for the Nonwovens and Related Industries," 2008 edition (published by "EDANA, International Association Serving the Nonwovens and Related Industries," Cary, N.C., U.S.A. and "INDA, Association of the Nonwovens Fabrics Industry," Brussels, Belgium).

The absorbent pad further can comprise a diffusion layer. This layer facilitates diffusion of wound exudate in a horizontal manner within the absorbent core. This layer can be present on the proximal side of the absorbent core between the proximal layer of the envelope and the proximal surface of the absorbent core. The diffusion layer can also be present as a layer of material that envelopes the entire absorbent core. Preferably, the diffusion layer is a tissue surrounding the layer of absorbent material. In a preferred embodiment, this tissue is made from cellulose and has a weight of 15 to 20 g/m².

The envelope surrounding the absorbent core comprises a proximal layer that covers the proximal side of the absorbent core facing the wound in use, and a distal layer that covers the distal side of the absorbent core facing away from the wound in use. The first layer of the envelope extends over the proximal side of the absorbent core and the second layer of the envelope extends over the distal side of the absorbent core, each of them leaving a border area surrounding the absorbent core. The first and the second layer of the envelope of the absorbent pad are connected to each other by a connection line along the border area surrounding the absorbent core.

In a preferred embodiment the distribution layer is the proximal layer of the envelope surrounding the absorbent core.

The envelope comprises a first, proximal layer of a first liquid-permeable material and a second, distal layer of a material different from the material of the first layer.

In a preferred embodiment, the envelope comprises a first layer of a liquid-permeable material exhibiting hydrophilic properties. The material can comprise a material that exhibits hydrophilic properties by its chemical nature or can comprise a material originally exhibiting hydrophobic properties that is treated by a chemical or physical process to exhibit hydrophilic properties. Suitable processes for the hydrophilization of originally non-hydrophilic materials include electrochemical processes, flame treatment, corona treatment and plasma treatment.

Suitable materials can be cellulose, polyester, polyamide, polyethylene, polypropylene, or copolymers from two or more of the aforementioned materials. Preferably, the first layer of hydrophilic material comprises either a polypropylene nonwoven that has been treated physically in order to exhibit hydrophilic properties or it comprises a nonwoven comprising a mixture of viscose fibers and polyamide fibers. Preferred materials can be a nonwoven comprising 55% Polyamide and 45% viscose fibers having a weight of 37 g/m² purchased under the name M1526 from the company Freudenberg (Germany) or a nonwoven comprising 63% polypropylene and 37% viscose fibers having a weight of 45 g/m² purchased under the name 670532/2 from the company Freudenberg (Germany).

In a preferred embodiment, the envelope comprises a second layer of a material exhibiting hydrophobic properties. The material can exhibit hydrophobic properties by its chemical nature or can comprise material originally exhibiting hydrophilic properties that is provided with hydrophobic properties by chemical or physical treatment, e.g. by the treatment with fluorocarbons, silicones, alkanes etc.

In a further preferred embodiment, the second layer of the envelope comprises a substantially liquid-impermeable material.

Both layers of the envelope surrounding the absorbent core can be colored in any way that is suitable. Usually, medical products have a white color signaling cleanness and purity. In one embodiment, one or both layers have a slightly green color. This color provides a strong color contrast when wetted with wound exudate, enabling the nurse staff to immediately recognize when the absorption capacity of the wound dressing has been reached. Surprisingly it has been found that a green color similar to RAL6019 provides the strongest color contrast with wound exudate while simultaneously signaling cleanness and purity.

The first and the second layer of the envelope of the absorbent pad are joined to each other. This joining can be formed by any suitable process for the joining of materials, directly or indirectly.

In a preferred embodiment the first and the second layer of the envelope each comprise a material exhibiting thermoplastic properties. It is possible to join the first layer and the second layer by a thermic process. Thermic processes for the joining of materials can be performed in a continuous manner and therefore can be more cost-effective than other procedures. Suitable thermic processes for the connection of materials include heat welding, laser welding and ultrasonic welding.

In a preferred embodiment the second layer of the envelope comprises a thermoplastic material that has hydrophobic properties and the first layer of the envelope comprises a thermoplastic material that is the same material as in the first layer and that has been treated chemically and/or physically to exhibit hydrophilic properties. If the first and the second layer comprises materials of different chemical nature, the physical properties of these materials can differ significantly. This can be disadvantageous in a joining process where conditions must be found that are compatible for each of the materials. In a thermic joining process the temperature must be higher than the melting points of each material. However, thermally sensitive materials can degrade during this procedure if the process temperature is too high.

Therefore, depending on the chemical nature of the materials of the first and the second layer the choice of manufacturing processes may be severely restricted. If the first and the second layer comprise a material that has the same chemical nature, the materials do not differ in their physical properties relevant for a connection procedure. This is especially advantageous in a thermic joining process, when the process temperature only has to be slightly above the softening temperature of the material, and the risk for thermally degradation of the material is significantly reduced.

In a preferred embodiment the thermoplastic material of both the first layer and the second layer comprises polypropylene.

In a preferred embodiment the first layer and the second layer of the envelope surrounding the envelope have been joined by a thermic process and therefore comprise a welding connection. A welding connection resulting from a thermic joining process exhibits a favorable connection characterized by its welding strength and its flexibility. Welding strength within the meaning of this application is the force that is necessary to separate two layers that are joined with each other. Welding strength can be determined by a method described below in the example part of this application. In a preferred embodiment the welding strength is higher than 0.75N/15 mm, preferably higher than 1N/15 mm.

A high welding strength is advantageous in order to prevent undesired delamination of the joined materials. Delamination of the first and the second layer of the absorbent core even in a minor extent can cause leakage. In that case wound exudate that has already been absorbed within the absorbent core could diffuse in outer zones of the wound dressing. It could contact intact skin surrounding the wound via a passage through the perforations in the wound contacting layer or it could leak from the wound dressing. This can cause maceration of intact skin surrounding the wound area. Furthermore, a leakage of wound exudate would cause a weakening of the adhesive connection between the backing layer and the perforated wound contact layer. If the leaked wound exudate diffuses along the distal side of the absorbent core that can cause the formation of wrinkles in the backing material which causes a discomfortable feeling for the user.

Flexibility within the meaning of this application is the property that enables a material to bend and to change its conformation. It is characterized by the stiffness.

Flexibility is important for the dressing to be able to adapt to an irregular body surface. Furthermore, a non-flexible dressing is very stiff and causes pressure on the patient's body surface during movement resulting in discomfort or pain.

In a preferred embodiment the welding connection comprises at least one non-continuous welding line. A non-continuous welding line exhibits a flexibility which is favorable for the patient's comfort.

In a preferred embodiment, the welding connection comprises four to six parallel non-continuous welding lines resulting in a favorably balanced relationship of both properties, welding strength and flexibility.

In a preferred embodiment the at least one welding line is arranged parallel to the machine direction of the manufacturing process.

The wound contact layer comprises a layer of skin-friendly silicone adhesive. Suitably, the silicone composition is a so-called soft skin adhesive silicone elastomer. The total coating weight of the silicone is suitably from about 15 g/m² to about 500 g/m², preferably 50 g/m² to 250 g/m², more preferably 100 g/m² to 200 g/m².

Surprisingly it has been found that a wound dressing according to claim 1 exhibits advantageous properties in the adhesive peel tests on skin described below in the example part of this application. A proper wound dressing must adhere to the skin without losing adhesiveness, which allows a use of the dressing for several hours, preferably for at least one day, more preferably for at least three days, most preferably for up to seven days. On the other hand, the dressing must exhibit skin-friendly properties that allow the dressing to be removed without causing pain to the patient or irritation to the wound or the surrounding skin. Surprisingly, it has been found that a dressing exhibiting a peel value on skin of between 200 mN/cm, preferably 350 mN/cm and 650 mN/cm is advantageous in this manner.

Although it is possible to provide a wound contact layer consisting essentially of a soft skin adhesive silicone elastomer, the wound contact layer preferably comprises a further layer of a perforated sheet material wherein the perforations of the sheet material correspond to the apertures of the silicone adhesive without being occluded by the silicone adhesive. The perforated sheet material may be any medically acceptable perforated sheet material, including textile materials. Suitably, the perforated sheet material is a unitary sheet material such as a polymer mesh or an apertured polymer film. Suitable polymer materials include polyethylene, polypropylene, polyester, polyvinyl acetate, ethylene vinyl acetate and polyurethane. Suitably, the sheet material has a thickness of 1 µm to 100 mm, preferably 5 µm to 50 µm. A preferred sheet material is a polyurethane material available under the tradename Acrysil® covered with 150 g/m² silicone adhesive from the company Zodiac (France).

The wound contact layer comprises apertures for the passage of wound exudate to the absorbent core. Apertures can have any geometrical shape, regular or irregular, in particular a circular, oval, triangular, square, rectangular, pentangular, hexagonal or other polygonal shape with uniform or non-uniform side length.

In a preferred embodiment the wound contact layer has an open area of between 10 to 30% of the entire area of the wound contact layer. Surprisingly it has been found that an open area in this range results in a favorable absorption velocity of wound exudate. Absorption velocity within the meaning of this application means the time of the absorption of wound exudate. It can be determined by a test method described in the example part of this application. The plurality of apertures each have an area of more than 4 mm² and less than 5 mm².

In a preferred embodiment the wound contact layer comprises apertures of any of these shapes having an average open area of from 0,03 mm² to 7,0 mm².

In a preferred embodiment the wound contact layer comprises apertures having an essentially circular shape and having an average diameter of between 0.2 mm to 3.0 mm. Surprisingly it has been found that the absorption velocity is favorable for a wound contact layer comprising apertures having a circular shape and an average diameter of 2.2 mm to 2.8 mm.

Suitably, the open area of the aperture layer is from about 10% to 30%. Surprisingly it has been found that the absorption velocity is favorable for a wound contact layer having an open area of 11% to 22%, preferably 12% to 18%. Suitably, the density of the apertures is from about 1000 to 100000 apertures per m², for example about 5000 to 50000 apertures per m².

Surprisingly it has been found that a wound dressing according to claim 1 exhibits advantageous properties in the absorption velocity test which is described below in the example part of this application.

Surprisingly, it has been found that a wound dressing according to claim 1 exhibits advantageous properties in respect to the balance between adhesiveness to skin and absorption velocity.

The backing layer, the absorbent pad and the wound contact layer can have different or similar extensions.

In one embodiment the dressing comprises a backing layer and an absorbent pad having a proximal and a distal surface. The distal surface of the absorbent pad is covered by the backing layer. The backing layer has an extension in both area directions that is larger than the area of the distal surface of the absorbent pad, while the absorbent pad and the wound contact layer are co-extensive. The backing layer therefore forms a border area completely surrounding the absorbent pad. The surrounding border area can be covered with a skin-friendly adhesive in order to build a dressing having a central absorbent pad and an adhesive border. This type of dressing is called "island-type" dressing.

In another embodiment the dressing comprises a backing layer and an absorbent pad having a proximal and a distal surface. The distal surface of the absorbent pad is covered by the backing layer. The backing layer has an extension in both area directions that is larger than the area of the distal surface of the absorbent pad, while the wound contact layer and the backing layer are co-extensive. This type of dressing is called "sandwich-type" dressing. The latter type of dressing has a lower risk for delamination.

In a preferred embodiment the absorbent core exhibits an absorption capacity of at least 100 g/100 cm², preferably more than 120 g/100 cm², more preferably more than 130 g/100 cm² according to the test method described within the example part of this application.

In a preferred embodiment the absorbent core comprises a mixture of absorbent fibers and superabsorbent materials. Absorbent fibers cause a quick absorption of wound exudate while superabsorbent materials exhibit a high absorption capacity. Suitable absorbent fibers can be cellulose-derived materials. In a preferred embodiment the absorbent fibers consist essentially of cellulose fibers. Suitable superabsorbent materials can be in the form of particles, gels or fibers. If the superabsorbent material is in the form of fibers, the fibers can be loosely distributed within the absorbent fibers or can be in a textile material. The textile material can comprise solely superabsorbent fibers or can further comprise absorbent fibers. The textile material can be in the form of any textile material that is suitable for incorporation into a wound dressing, e.g. nonwovens, woven, warp-knitted or weft-knitted materials.

In a preferred embodiment the absorbent core comprises a mixture of absorbent fibers and superabsorbent particles.

The wound dressing, the backing layer, the absorbent core, the absorbent pad, the envelope and the wound contact layer each can have any suitable size and basic geometrical shape, particularly squares, rectangles, circles, ovals, polygons. If the basic geometrical shape of any of these layers comprises corners, these corners preferably are rounded. This reduces the risk of curling of the layer and of delamination from other layers or skin. In a preferred embodiment, the radius for the rounded corners is from 5 mm to 15 mm, more preferably 12.5 mm.

In a preferred embodiment the first layer of the envelope and the second layer of the envelope are joined along the border area surrounding the absorbent core in a joining area, the joining area having an inner margin and an outer margin, and that the envelope comprises a space between the first and the second layer of the envelope, wherein the absorbent core is placed, the space being limited by the inner margin of the joining area, and the space having an area $A_1$, the absorbent core having an area $A_2$, wherein the area $A_2$ is at least 80% of the area $A_1$.

The dressing according to the present invention may further comprise at least one removable cover sheet to cover the adhesive areas on the proximal surface of the wound dressing. The cover sheet covers and protects the absorbent pad and prevents premature adhesion of the adhesive parts of the wound dressing. It may comprise a film of polyethylene, polypropylene or fluorocarbons and paper coated with these materials or silicone. A suitable material for a cover sheet can be a polyethylene foil having a thickness of 100 µm and can be purchased from the company Flextrus®.

Figure 1:
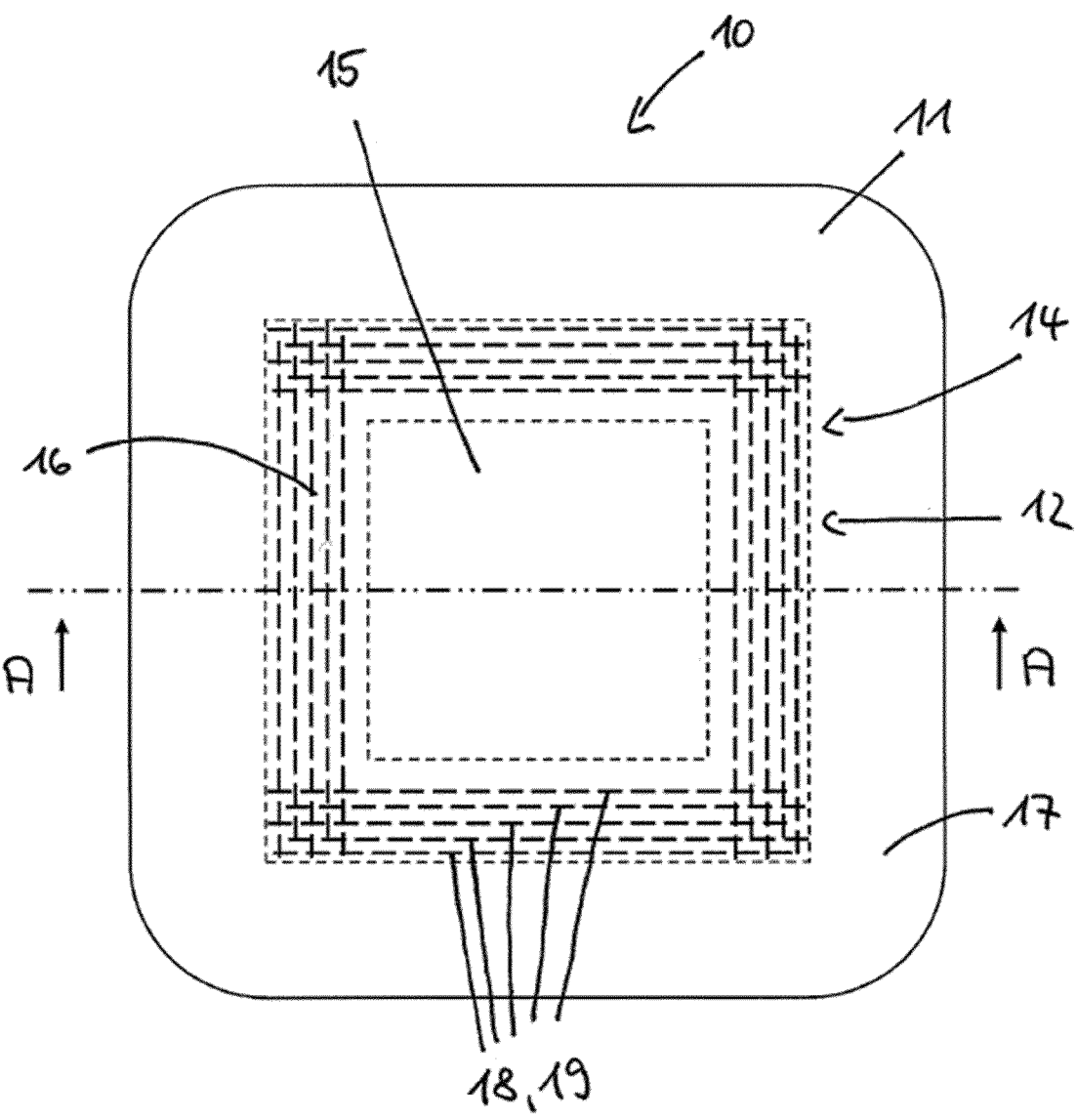
FIG. 1 shows a wound dressing in a top view representing a sandwich-type embodiment of the invention.

FIG. 1 shows a top view of a wound dressing (10) having a backing layer (11) and an absorbent pad (12), wherein the backing layer (11) covers the distal side of the absorbent pad (12) and extends over the distal side of the absorbent pad (12), thereby forming a border area (17) surrounding the absorbent pad (12). A wound contact layer is present on the side of the dressing facing away from the viewer. The absorbent pad (12) comprises an absorbent core (15) and an envelope (14) surrounding the absorbent core (15). The envelope (14) comprises a first, proximal layer (facing away from the viewer) of a liquid-permeable nonwoven material as distribution layer and a second, distal layer (14b, see FIG. 2) of a substantially liquid-impermeable nonwoven material. The proximal layer of the envelope (14) covers the proximal side of the absorbent core (15) and extends over the proximal side of the absorbent core (15), thereby forming a border area (16) surrounding the absorbent core (15). The distal layer (14b) of the envelope (14) covers the distal side of the absorbent core (15) and extends over the distal side of the absorbent core (15), thereby forming a border area (16) surrounding the absorbent core (15). The proximal layer of the envelope (14) and the distal layer (14b) of the envelope (14) are joined along the border area (16) surrounding the absorbent core (15) by a thermic process and therefore comprise a welding connection (18). The welding connection (18) is formed from five non-continuous welding lines (19).

Figure 2:
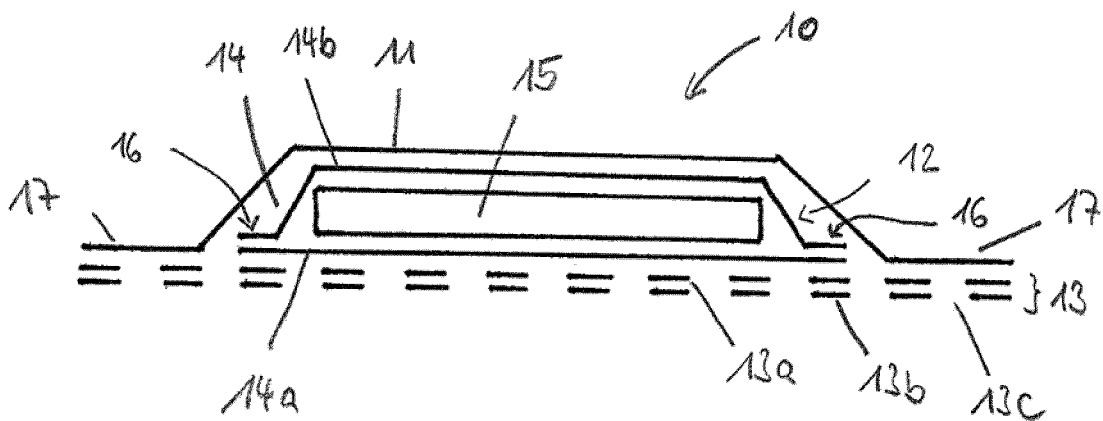
FIG. 2 shows the wound dressing of FIG. 1 in a cross-section view along the cutting line A-A.

FIG. 2 shows the wound dressing (10) of FIG. 1 in a cross-sectional view along the cutting line A-A of FIG. 1. The wound dressing (10) represents a sandwich-type dressing having an absorbent pad (12), a backing layer (11) and a wound contact layer (13). The absorbent pad (12) comprises an absorbent core (15) and an envelope (14). The envelope (14) is formed from a proximal layer (14a) and a distal layer (14b). The proximal layer (14a) of the envelope (14) is a distribution layer. The wound contact layer (13) is formed from a layer of a perforated sheet material (13a) and a layer of skin-friendly silicone adhesive (13b). The backing layer (11) is made from a vapour-permeable and liquid-impermeable polyurethane film material with low friction characteristics having a thickness of 30 µm. The backing layer (11) is coated with a layer of acrylate-based adhesive (not shown). The absorbent core (15) comprises a mixture of cellulose fibers and superabsorbent sodium polyacrylate particles in a pre-fabricated airlaid material. The absorbent core (15) further comprises a diffusion layer (not shown) in form of a sheet of cellulose tissue that is wrapped around the airlaid mixture of cellulose fibers and polyacrylate particles.

The proximal layer (14a) of the envelope (14) is a nonwoven made from a mixture of viscose fibers and polyamide fibers. The distal layer (14b) of the envelope (14) is a nonwoven made from polypropylene fibers. The proximal layer (14a) of the envelope (14) covers the proximal side of the absorbent core (15) and extends over the proximal side of the absorbent core (15), thereby forming a border area (16) surrounding the absorbent core (15). The distal layer (14b) of the envelope (14) covers the distal side of the absorbent core (15) and extends over the distal side of the absorbent core (15), thereby forming a border area (16) surrounding the absorbent core (15). The proximal layer (14a) of the envelope (14) and the distal layer (14b) of the envelope (14) are joined along the border area (16) surrounding the absorbent core (15). The perforated sheet material (13a) of the wound contact layer (13) is made from a polyurethane film that comprises apertures (13c) having a circular shape. These apertures (13c) have similar shapes having an average diameter of 2.4 mm and are arranged in a regular pattern resulting in an open area of 15%. The backing layer (11) extends over the absorbent pad (12), thereby forming a border surrounding the absorbent pad (12). The wound contact layer (13) extends over the absorbent pad (12), thereby forming a border area (17) surrounding the absorbent pad (12). The backing layer (11) and the wound contact layer (13) are coextensive.

Figure 3:
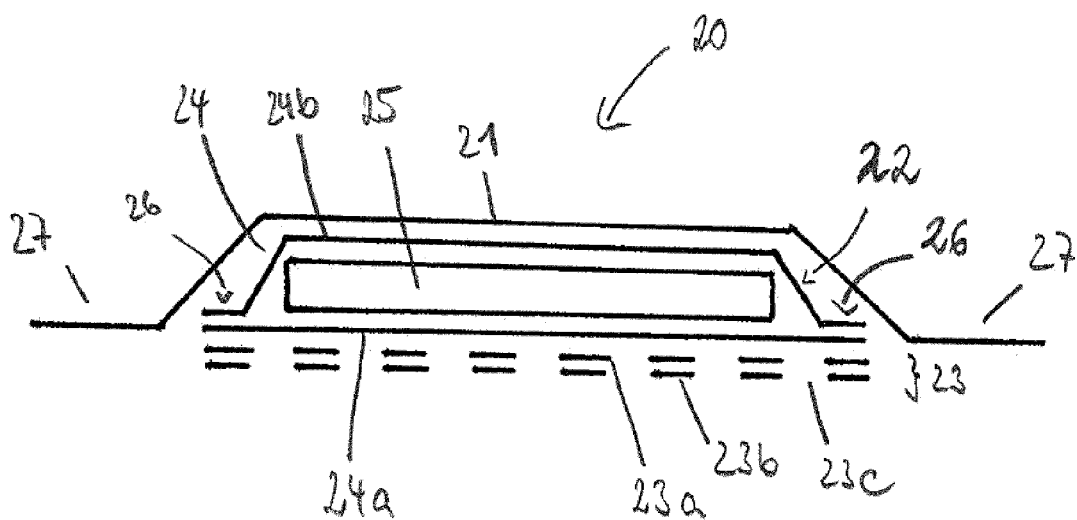
FIG. 3 shows a wound dressing in a cross-section view of an island-type embodiment of the invention.

FIG. 3 shows a wound dressing (20) of an island-type having an absorbent pad (22), a backing layer (21) and a wound contact layer (23). The absorbent pad (22) comprises an absorbent core (25) and an envelope (24). The envelope is formed from a proximal layer (24a) and a distal layer (24b). The proximal layer (24a) of the envelope (24) is a distribution layer. The wound contact layer (23) is formed from a layer of a perforated sheet material (23a) and a layer of skin-friendly silicone adhesive (23b). The backing layer (21) is made from a vapour-permeable and liquid-impermeable polyurethane film material with low friction characteristics having a thickness of 30 µm. The backing layer (21) is coated with a layer of acrylate-based adhesive (not shown). The absorbent core (25) comprises a mixture of cellulose fibers and superabsorbent sodium polyacrylate particles in a pre-fabricated airlaid material. The absorbent core (25) further comprises a diffusion layer (not shown) in form of a sheet of cellulose tissue that is wrapped around the airlaid mixture of cellulose fibers and polyacrylate particles. The proximal layer (24a) of the envelope (24) is a nonwoven made from a mixture of viscose fibers and polyamide fibers. The distal layer (24b) of the envelope (24) is a nonwoven made from polypropylene fibers. The proximal layer (24a) of the envelope (24) covers the proximal side of the absorbent core (25) and extends over the proximal side of the absorbent core (25), thereby forming a border area surrounding the absorbent core (25). The distal layer (24b) of the envelope (24) covers the distal side of the absorbent core (25) and extends over the distal side of the absorbent core (25), thereby forming a border area (26) surrounding the absorbent core (25). The proximal layer (24a) of the envelope (24) and the distal layer (24b) of the envelope (24) are joined along the border area (26) surrounding the absorbent core (25). The perforated sheet material (23a) of the wound contact layer (23) is made from a polyurethane film that comprises apertures (23c) having a circular shape. These apertures (23c) have similar shapes having an average diameter of 2.4 mm and are arranged in a regular pattern resulting in an open area of 15%. The wound contact layer further comprises a layer of skin-friendly silicone adhesive (23b). The backing layer (21) extends over the absorbent pad (22), thereby forming a border area (27) surrounding the absorbent pad (22).

EXAMPLES

Example 1: Wound Dressing

The wound dressing has an absorbent pad, a backing layer and a wound contact layer. The absorbent pad comprises an absorbent core and an envelope. The envelope is formed from a proximal layer and a distal layer. The wound contact layer is formed from a layer of a perforated sheet material and a layer of skin-friendly silicone adhesive. The backing layer is made from a vapour-permeable and liquid-impermeable polyurethane film material with low friction characteristics having a thickness of 30 μm. The absorbent core comprises a mixture of cellulose fibers and superabsorbent sodium polyacrylate particles in a pre-fabricated airlaid material. The absorbent core further comprises a diffusion layer in form of a sheet of cellulose tissue that is wrapped around the airlaid mixture of cellulose and polyacrylate particles. The proximal layer of the envelope is a nonwoven made from a mixture of viscose and polyamide fibers. The distal layer of the envelope is a nonwoven made from polypropylene fibers. The perforated sheet material of the wound contact layer is made from a polyurethane film that comprises apertures having a circular shape. These apertures exhibit similar shapes having an average diameter of 2.4 mm and are arranged in a regular pattern resulting in an open area of 15%. The wound contact layer further comprises a layer of skin-friendly silicone adhesive without occluding the apertures of the perforated sheet material.

Example 2: Test Solutions Used in the Characterization of Wound Dressings

Solution A (Saline Solution)
  2L Deionized water
  0,74 g Calcium chloride dihydrate (CaCl$_2$)·2 H$_2$O, CAS: 10035 Apr. 5)
  16,6 g Sodium chloride (NaCl, CAS: 7647-14-5)
Solution B (Exudates Solution)
  1 L Deionized water
  70 g Albumin from chicken egg white (N° CAS 9006-59-1)
  0,2 g Allura Red AC (CAS 25956-17-6)
  9 g Sodium chloride (NaCl, N° CAS: 7647-14-5)
  0,37 g Calcium chloride dihydrate (CaCl$_2$)·2 H$_2$O, N° CAS: 10035 Apr. 5)
  2 g Methyl 4-hydroxybenzoate (CAS: 99-76-3)
  1 g Propyl 4-hydroxybenzoate (CAS: 94-13-3)

Example 3: Test Method Absorption Velocity

The absorption velocity of a dressing is determined by the time necessary to completely absorb a test solution. Test solutions can be either saline solution (solution A) or exudate solution (solution B). Solutions (saline solution or exudates solution) as well as test products must be preconditioned at room temperature prior to testing by leaving the test products and the solutions for two hours at 22° C.

A 50 mL buret is filled with the test solution. The liquid level should be fixed at 15 mL. The dressing is placed under the buret, that surface which in use faces the wound now faces the buret. The distance between the buret and the dressing is adjusted to 1 cm. The tap of the buret is opened, and simultaneously a stopwatch is started, while 2 mL of test solution are allowed to flow out. The stopwatch is stopped immediately when the 2 mL of test solution are completely absorbed by the dressing, i.e. when no drop is remaining over the perforation of the wound contact layer. If the dressing is big enough, 1 to 3 measurements can be made on the same dressing.

Positions of the tests on a dressing are one in the centre, two further points along a diagonal in direction to the corners of the dressing, similar to the position of the three points on a regular die.

At least five samples have to be investigated.

Each value has to be classified in the following categories

| Time (s) | [0 to 4.9] | [5.0 to10.9] | [11.0 to 30.9] | [31.0 to 60.0] | >60 |
|---|---|---|---|---|---|
| category | Immediate | Very quick | quick | Average | slow |

A dressing according to the invention has been compared with commercially available competitor dressings Biatain® silicone, Allevyn® Life, Mepilex® border (which is considered as being a dressing according to the disclosure of WO93/19709 and WO93/19710).

| | Absorption velocity: | | | | |
|---|---|---|---|---|---|
| | Absorption velocity [percentage of samples] | | | | |
| Dressing | immediate | Very quick | quick | average | slow |
| Example 1 | 20% | 80% | 0% | 0% | 0% |
| Biatain ® silicone | 0% | 0% | 0% | 20% | 80% |
| Allevyn ® Life | 0% | 0% | 100% | 0% | 0% |
| Mepilex ® border | 0% | 0% | 0% | 100% | 0% |

Example 4: Test Method Absorption Capacity

Solutions (saline solution or exudates solution) as well as test products must be preconditioned at room temperature prior to testing by leaving the test products and the test solutions for two hours at 22° C.

The basic mass (m$_1$) of a dressing is determined after removal of the release liners. The length and width of the absorbent core is determined so that the absorbent core surface(S) can be determined. A bowl is filled with the test solution. The weight of testing solution should be at least 40 times higher than the dressing itself. The dressing is put into the bowl, and simultaneously a stopwatch is started. That side of the dressing which in use faces the wound side should face the bottom of the bowl, the back side of the dressing should be on the top. The dressing should not be glued to the bottom of the bowl. The dressing is left within the bowl for 30 min +/−1 min. After 30 min, the dressing is removed from the bowl. The dressings should only be manipulated via the borders and not the absorbent core itself. The dressings are fixed on one corner to a stand with a clamp and allowed to hang for 20 min at room temperature. The wet mass (m$^2$) of the dressing is determined. The amount of liquid (m$_{liquid}$) absorbed is calculated:

$$m_{liquid} = m^2 - m_1$$

The absorption capacity is the amount of liquid absorbed (m$_2$−m$_1$) by the absorbent core surface(S) and is given in g/100 cm$^2$:

$$\text{absorption capacity} = m^2 - m_1 / S \times 100$$

A dressing according to the invention has been compared with commercially available competitor dressings Biatain® silicone, Allevyn® Life, Mepilex® border (which is considered as being a dressing according to the disclosure of WO93/19709 and WO93/19710).

| Comparison of absorption capacities: | |
| --- | --- |
| Dressing | Absorption capacity in g/100 cm² |
| Example 1 | 147 |
| Biatain ® silicone | 116 |
| Allevyn ® Life | 87 |
| Mepilex ® border | 54 |

Example 5: Test Method for Adhesiveness on Skin-Peel Test

Subjects came to the Study Site. They were informed about the study and gave their written consent. Test products were applied to the back of each subject (two samples per test product): One sample of each test product was adhered to the upper part of the back. The second sample of each test product was adhered to the lower part of the back at the same position as the first sample in the upper part.

The lower end of each sample was folded on the length of approximately 0.5 cm, in order to obtain a starting point for removing the sample from downside to upside with the universal test machine. The test materials were applied by a technician and pressed to the skin with the use of a metal roll (1 kg, 5 times of rolling back and forth).

Subjects came to the Study Site 3 hours and 50 minutes after the product application. They stayed in the air-conditioned room for at least 10 minutes. It was checked that the subjects did not sweat. Then, samples were removed 4 hours after application by using a universal test machine, set up for determining adhesive forces.

Universal Test Machine: Zwick 1120 (Zwick GmbH, Ulm, Germany). The universal test machine measures the force needed to pull off the adhesive-coated backings from the skin.

For removal of the samples the subjects were positioned in a sitting position. The samples were removed under an angle of approximately 135° 1 measurement per sample, 2 samples per product

Example 6: Test Method for Welding Strength

The test for welding strength is carried out with Tensile Tester MTS C42.503E (MTS Systems Corporation, Eden Prairie, USA); cell strength 50N.

Test samples are prepared by stamping a part of the absorbent pad including the welding line having a rectangular shape of 15 mm in width and 25 mm in length, wherein the 15 mm side corresponds to the welding line. The sample must be at a distance of at least 2 mm from the corner. After stamping, the absorbent material is removed. The sample to be tested is only made of 2 nonwovens welded together. The clamp jaws of the tensile tester are placed in a way that the distance between the 2 jaws is 2 cm. Each nonwoven is placed in a separate jaw. The tensile tester is started at a speed of 200 mm/min until the 2 nonwovens are separated. This can happen either after a complete break of the weld or after complete tearing of the nonwovens themselves.

The welding strength is the average strength over the testing period. It is given in N/15 mm.

The invention claimed is:

1. A wound dressing (10, 20) comprising a backing layer (11, 21), an absorbent pad (12, 22) and a wound contact layer (13, 23), the absorbent pad (12, 22) having an absorbent core (15, 25), wherein the backing layer (11, 21) comprises a water vapour-permeable and liquid-impermeable film material, wherein the entire wound contact layer (13, 23) comprises a layer of skin-friendly silicone adhesive (13*b*, 23*b*), the wound contact layer (13, 23) comprising a plurality of apertures (13*c*, 23*c*), each of the plurality of apertures (13*c*, 23*c*) having an average area of from 0.03 mm² to 7.00 mm², and an entire open area of the wound contact layer (13, 23) formed by the plurality of apertures (13*c*, 23*c*) is between 10% and 30%, characterized in that a distribution layer (14*a*, 24*a*) is arranged between the wound contact layer (13, 23) and the absorbent core (15, 25), wherein the distribution (14*a*, 24*a*) layer comprises a nonwoven material, and wherein the distribution (14*a*, 24*a*) layer and the wound contact layer (13, 23) are joined to each other and, wherein the absorbent pad (12, 22) comprises an envelope (14, 24) surrounding the absorbent core (15, 25) and wherein the envelope (14, 24) comprises a proximal layer (14*a*, 24*a*) covering a proximal side of the absorbent core (15, 25) and a distal layer (14*b*, 24*b*) covering a distal side of the absorbent core (15, 25), each of them forming a border area (16, 26) surrounding the absorbent core (15, 25), wherein the proximal (14*a*, 24*a*) and distal layer (14*b*, 24*b*) of the envelope (14, 24) are joined to each other along the border area (16, 26) surrounding the absorbent core (15, 25), and wherein the distribution layer (14*a*, 24*a*) is the proximal layer (14*a*, 24*a*) of the envelope (14, 24) and wherein the proximal layer is a first liquid-permeable material and the distal layer is a second liquid-impermeable material and wherein one or both of the proximal layer and the distal layer have a green color of RAL6019;

wherein the first material is a non-woven liquid-permeable material and the second material is a non-woven liquid impermeable material; and wherein the backing layer (11, 21) is transparent to enable viewing of the envelope (14, 24) to determine a degree of wetness of the one or both of the proximal layer and the distal layer based at least in part on a presence of a color contrast provided by the green color of RAL6019.

2. The wound dressing (10, 20) of claim 1, wherein the absorbent pad can further comprise a diffusion layer.

3. The wound dressing (10, 20) of claim 2, wherein the diffusion layer comprises tissue.

4. The wound dressing (10, 20) of claim 3, wherein the tissue comprises cellulose.

5. The wound dressing (10, 20) of claim 4, wherein the cellulose has a weight of to 20 g/m².

6. The wound dressing recited in claim 2, wherein the diffusion layer is made from cellulose having a weight of 15 to 20 g/m².

7. The wound dressing (10, 20) of claim 2, wherein the diffusion layer is a layer of material that envelops the entire absorbent core.

8. The wound dressing recited in claim 1, wherein the proximal layer and the distal layer are joined by a thermic process to form a welding connection between the proximal layer and the distal layer.

9. The wound dressing recited in claim 8, wherein the welding connection comprises at least one non-continuous welding line.

10. The wound dressing (10, 20) of claim 1, wherein the wound contact layer (13, 23) comprises the layer of skin-friendly silicone adhesive (13*b*, 23*b*) in an amount from 100 g/m² to 200 g/m².

11. The wound dressing (10, 20) of claim 1, wherein the wound dressing (10, 20) is configured to have an adhesion on skin from 200 mN/cm to 650 mN/cm.

12. The wound dressing (10, 20) of claim 1, wherein the plurality of apertures (13*c*, 23*c*) each have an area of more than 4 mm² and less than 5 mm², the entire open area formed by the plurality of apertures (13*c*, 23*c*) being from 12% to 18%.

13. The wound dressing (10, 20) of claim 1, wherein the absorbent pad material comprises a mixture of absorbent fibers and absorbent particles.

14. The wound dressing recited in claim 1, wherein the non-woven liquid impermeable material comprises propylene fibers.

15. The wound dressing recited in claim 11, wherein the wound contact layer is connected to the proximal layer by a polyacrylate-based pressure-sensitive adhesive.

16. The wound dressing recited in claim 1, wherein the wound contact layer comprises a polyurethane sheet material coupled to the silicone adhesive, the polyurethane sheet material having a plurality of openings that are aligned with the plurality of apertures.

17. A wound dressing comprising:

a backing layer;

a wound contact layer opposite the backing layer;

an envelope positioned between the backing layer and the wound contact layer; and an absorbent core positioned within the envelope, wherein the backing layer comprises a vapor-permeable and liquid-impermeable material, wherein the entire wound contact layer comprises silicone adhesive, wherein the envelope comprises opposite proximal and distal layers, the proximal layer comprising a first material, the distal layer comprising a second material, the second material being different than the first material, and wherein one or both of the proximal layer and the distal layer have a green color of RAL6019, and wherein the first material is a non-woven liquid-permeable material and the second material is a non-woven liquid impermeable material, wherein the non-woven liquid-permeable material comprises a mixture of polypropylene and viscose fibers, wherein the wound contact layer is connected to the proximal layer by a polyacrylate-based pressure-sensitive adhesive, wherein an absorption capacity of the proximal layer is less than 20% of an absorption capacity of the absorbent pad, and wherein the wound contact layer comprises a plurality of apertures extending through the silicone adhesive and a polyurethane sheet material coupled to the silicone adhesive, the polyurethane sheet material having a plurality of openings that are aligned with the plurality of apertures;

wherein the backing layer (11, 21) is transparent to enable viewing of the envelope (14, 24) to determine a degree of wetness of the one or both of the proximal layer and the distal layer based at least in part on a presence of a color contrast provided by the green color of RAL6019.

18. The wound dressing of claim 17, further comprising a diffusion layer present on a proximal side of the absorbent core between the proximal layer of the envelope and a proximal surface of the absorbent core.

* * * * *